(12) United States Patent
Vitello et al.

(10) Patent No.: US 11,872,187 B1
(45) Date of Patent: Jan. 16, 2024

(54) TAMPER EVIDENT SEAL FOR A VIAL COVER

(71) Applicants: Jonathan Vitello, Pompano Beach, FL (US); Peter Lehel, Boca Raton, FL (US)

(72) Inventors: Jonathan Vitello, Pompano Beach, FL (US); Santiago Paredes, Pompano Beach, FL (US); Peter Lehel, Boca Raton, FL (US)

( * ) Notice: Subject to any disclaimer, the term of this patent is extended or adjusted under 35 U.S.C. 154(b) by 0 days.

(21) Appl. No.: 17/563,371

(22) Filed: Dec. 28, 2021

Related U.S. Application Data

(60) Provisional application No. 63/131,124, filed on Dec. 28, 2020.

(51) Int. Cl.
| | | |
|---|---|---|
| *A61J 1/14* | (2023.01) | |
| *B65D 51/24* | (2006.01) | |
| *B65D 41/46* | (2006.01) | |

(52) U.S. Cl.
CPC .......... *A61J 1/1425* (2015.05); *B65D 41/465* (2013.01); *B65D 51/245* (2013.01); *A61J 2205/10* (2013.01)

(58) Field of Classification Search
CPC ... A61J 1/1425; A61J 2205/10; B65D 41/465; B65D 51/245
USPC ....................................................... 220/212
See application file for complete search history.

(56) References Cited

U.S. PATENT DOCUMENTS

| | | |
|---|---|---|
| 722,943 A | 3/1903 | Chappell |
| 732,662 A | 6/1903 | Smith |
| 1,678,991 A | 7/1928 | Marschalek |
| 1,970,631 A | 8/1934 | Sherman |
| 2,477,598 A | 8/1949 | Hain |
| 2,739,590 A | 3/1956 | Yochem |
| 2,823,674 A | 2/1958 | Yochem |
| 2,834,346 A | 5/1958 | Adams |
| 2,875,761 A | 3/1959 | Helmer et al. |
| 2,888,015 A | 5/1959 | Hunt |
| 2,952,255 A | 9/1960 | Hein, Jr. |
| 3,122,280 A | 2/1964 | Goda |

(Continued)

FOREIGN PATENT DOCUMENTS

| | | |
|---|---|---|
| DE | 202008018507 | 2/2015 |
| EP | 0148116 | 7/1985 |

OTHER PUBLICATIONS

Arai Tsugio, Pilfering Proof Cap, Jan. 1, 1996.

*Primary Examiner* — J. Gregory Pickett
*Assistant Examiner* — Niki M Eloshway
(74) *Attorney, Agent, or Firm* — Malloy & Malloy, PL; Jennie S. Malloy

(57) ABSTRACT

A tamper evident seal structure for a vial septum or other cover having a housing including a sidewall terminating in oppositely disposed open and closed ends. A retainer is fixedly disposed within the housing and structured for retaining engagement with a portion of a vial, substantially adjacent the vial cover. The housing also includes a pressure member disposed within an interior thereof in attached, relation to the closed-end. The pressure member and the retainer are cooperatively disposed and structured to respectively exert pressure on the vial cover concurrent to retaining engagement with the vial. Tamper evident capabilities are at least partially defined by a detachment of a removable sidewall section from a remainder of said sidewall.

20 Claims, 2 Drawing Sheets

(56) References Cited

U.S. PATENT DOCUMENTS

| | | |
|---|---|---|
| 3,245,567 A | 4/1966 | Knight |
| 3,323,798 A | 6/1967 | Miller |
| 3,364,890 A | 1/1968 | Andersen |
| 3,368,673 A | 2/1968 | Johnson |
| 3,489,268 A | 1/1970 | Meierhoefer |
| 3,574,306 A | 4/1971 | Alden |
| 3,598,120 A | 8/1971 | Mass |
| 3,610,241 A | 10/1971 | LeMarie |
| 3,674,181 A | 7/1972 | Marks et al. |
| 3,700,215 A | 10/1972 | Hardman et al. |
| 3,706,307 A | 12/1972 | Hasson |
| 3,712,749 A | 1/1973 | Roberts |
| 3,726,445 A | 4/1973 | Ostrowsky et al. |
| 3,747,751 A | 7/1973 | Miller et al. |
| 3,850,329 A | 11/1974 | Robinson |
| 3,872,867 A | 3/1975 | Killinger |
| 3,904,033 A | 9/1975 | Haerr |
| 3,905,375 A | 9/1975 | Toyama |
| 3,937,211 A | 2/1976 | Merten |
| 3,987,930 A | 10/1976 | Fuson |
| 4,005,739 A | 2/1977 | Winchell |
| 4,043,334 A | 8/1977 | Brown et al. |
| 4,046,145 A | 9/1977 | Choksi et al. |
| 4,068,696 A | 1/1978 | Winchell |
| 4,106,621 A | 8/1978 | Sorenson |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,271,972 A | 6/1981 | Thor |
| 4,286,591 A | 9/1981 | Raines |
| 4,286,640 A | 9/1981 | Knox et al. |
| 4,313,539 A | 2/1982 | Raines |
| 4,369,781 A | 1/1983 | Gilson et al. |
| 4,420,085 A | 12/1983 | Wilson et al. |
| 4,430,077 A | 2/1984 | Mittleman et al. |
| 4,457,445 A | 7/1984 | Hanks et al. |
| 4,482,071 A | 11/1984 | Ishiwatari |
| D277,783 S | 2/1985 | Beck |
| 4,521,237 A | 6/1985 | Logothetis |
| 4,530,697 A | 7/1985 | Kuhlemann et al. |
| 4,571,242 A | 2/1986 | Klien et al. |
| 4,589,171 A | 5/1986 | McGill |
| 4,664,259 A | 5/1987 | Landis |
| 4,667,837 A | 5/1987 | Vitello et al. |
| 4,676,530 A | 6/1987 | Nordgren et al. |
| 4,693,707 A | 9/1987 | Dye |
| 4,726,483 A | 2/1988 | Drozd |
| 4,735,617 A | 4/1988 | Nelson et al. |
| 4,742,910 A | 5/1988 | Staebler |
| 4,743,229 A | 5/1988 | Chu |
| 4,743,231 A | 5/1988 | Kay et al. |
| 4,760,847 A | 8/1988 | Vaillancourt |
| 4,813,564 A | 3/1989 | Cooper et al. |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 4,936,445 A | 6/1990 | Grabenkort |
| 5,009,323 A | 4/1991 | Montgomery et al. |
| 5,024,323 A | 6/1991 | Bolton |
| 5,049,129 A | 9/1991 | Zdeb et al. |
| D323,392 S | 1/1992 | Bryne |
| 5,078,696 A | 1/1992 | Nedbaluk |
| 5,085,332 A | 2/1992 | Gettig et al. |
| 5,090,564 A | 2/1992 | Chimienti |
| 5,133,454 A | 7/1992 | Hammer |
| 5,135,496 A | 8/1992 | Vetter et al. |
| 5,163,922 A | 11/1992 | McElveen, Jr. et al. |
| 5,165,560 A | 11/1992 | Ennis, III et al. |
| 5,230,429 A | 7/1993 | Etheredge, III |
| 5,267,983 A | 12/1993 | Oilschlager et al. |
| 5,292,308 A | 3/1994 | Ryan |
| 5,293,993 A | 3/1994 | Yates, Jr. et al. |
| 5,295,599 A | 3/1994 | Smith |
| 5,312,367 A | 5/1994 | Nathan |
| 5,312,368 A | 5/1994 | Haynes |
| 5,328,466 A | 7/1994 | Denmark |
| 5,328,474 A | 7/1994 | Raines |
| 5,356,380 A | 10/1994 | Hoekwater et al. |
| 5,370,226 A | 12/1994 | Gollobin et al. |
| 5,380,295 A | 1/1995 | Vacca |
| 5,402,887 A | 4/1995 | Shillington |
| 5,405,339 A | 4/1995 | Kohnen et al. |
| 5,456,668 A | 10/1995 | Ogle, II |
| 5,458,580 A | 10/1995 | Hajishoreh |
| 5,468,224 A | 11/1995 | Souryal |
| 5,474,178 A | 12/1995 | DiViesti et al. |
| 5,505,705 A | 4/1996 | Galpin et al. |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,617,954 A | 4/1997 | Kato et al. |
| 5,624,402 A | 4/1997 | Imbert |
| 5,662,233 A | 9/1997 | Reid |
| 5,674,209 A | 10/1997 | Yarger |
| 5,695,470 A | 12/1997 | Roussigne et al. |
| 5,700,247 A | 12/1997 | Grimard et al. |
| 5,702,374 A | 12/1997 | Johnson |
| 5,713,485 A | 2/1998 | Lift et al. |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| 5,829,589 A | 11/1998 | Nguyen et al. |
| D402,766 S | 12/1998 | Smith et al. |
| 5,842,567 A | 12/1998 | Rowe et al. |
| 5,876,381 A | 3/1999 | Pond et al. |
| 5,883,806 A | 3/1999 | Meador et al. |
| 5,884,457 A | 3/1999 | Ortiz et al. |
| 5,902,269 A | 5/1999 | Jentzen |
| 5,926,922 A | 7/1999 | Stottle |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,957,314 A | 9/1999 | Nishida et al. |
| 5,963,136 A | 10/1999 | O'Brien |
| 5,989,227 A | 11/1999 | Vetter et al. |
| 5,993,437 A | 11/1999 | Raoz |
| 6,000,548 A | 12/1999 | Tsais |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| D431,864 S | 10/2000 | Jansen |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,216,885 B1 | 4/2001 | Guillaume |
| 6,279,746 B1 | 4/2001 | Hussaini et al. |
| 6,235,376 B1 | 5/2001 | Miyazaki et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,358,241 B1 | 3/2002 | Shapeton et al. |
| 6,375,640 B1 | 4/2002 | Teraoka |
| 6,394,983 B1 | 5/2002 | Mayoral et al. |
| 6,439,276 B1 | 8/2002 | Wood et al. |
| 6,485,460 B2 | 11/2002 | Eakins et al. |
| 6,488,666 B1 | 12/2002 | Geist |
| 6,491,665 B1 | 12/2002 | Vetter et al. |
| 6,500,155 B2 | 12/2002 | Sasso |
| 6,520,935 B1 | 2/2003 | Jansen et al. |
| 6,540,697 B2 | 4/2003 | Chen |

(56) References Cited

U.S. PATENT DOCUMENTS

| | | |
|---|---|---|
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. |
| 6,682,798 B1 | 1/2004 | Kiraly |
| 6,726,652 B2 | 4/2004 | Eakins et al. |
| 6,726,672 B1 | 4/2004 | Hanly et al. |
| 6,764,469 B2 | 7/2004 | Broselow |
| 6,796,586 B2 | 9/2004 | Werth |
| 6,821,268 B2 | 11/2004 | Balestracci |
| D501,549 S | 2/2005 | McAllister et al. |
| 6,921,383 B2 | 7/2005 | Vitello |
| 6,935,560 B2 | 8/2005 | Andreasson et al. |
| 6,942,643 B2 | 9/2005 | Eakins et al. |
| 7,036,661 B2 | 5/2006 | Anthony et al. |
| 7,055,273 B2 | 6/2006 | Roshkoff |
| 7,100,771 B2 | 9/2006 | Massengale et al. |
| 7,125,397 B2 | 10/2006 | Woehr et al. |
| 7,141,286 B1 | 11/2006 | Kessler et al. |
| 7,175,081 B2 | 2/2007 | Andreasson et al. |
| 7,182,256 B2 | 2/2007 | Andreasson et al. |
| 7,232,066 B2 | 6/2007 | Anderasson et al. |
| 7,240,926 B2 | 7/2007 | Dalle et al. |
| 7,299,981 B2 | 11/2007 | Hickle et al. |
| 7,374,555 B2 | 5/2008 | Heinz et al. |
| 7,404,500 B2 | 7/2008 | Marteau et al. |
| 7,410,803 B2 | 8/2008 | Nollert et al. |
| 7,425,208 B1 | 9/2008 | Vitello |
| 7,437,972 B2 | 10/2008 | Yeager |
| D581,046 S | 11/2008 | Sudo |
| D581,047 S | 11/2008 | Koshidaka |
| D581,049 S | 11/2008 | Sudo |
| 7,482,166 B2 | 1/2009 | Nollert et al. |
| D589,612 S | 3/2009 | Sudo |
| 7,497,330 B2 | 3/2009 | Anthony et al. |
| 7,503,453 B2 | 3/2009 | Cronin et al. |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |
| D608,900 S | 1/2010 | Giraud et al. |
| 7,641,636 B2 | 1/2010 | Moesli et al. |
| D612,939 S | 3/2010 | Boone, III et al. |
| 7,681,606 B2 | 3/2010 | Khan et al. |
| 7,698,180 B2 | 4/2010 | Fago et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,886,908 B2 | 2/2011 | Farrar et al. |
| 7,918,830 B2 | 4/2011 | Langan et al. |
| 7,922,213 B2 | 4/2011 | Werth |
| 8,034,041 B2 | 10/2011 | Domkowski et al. |
| 8,079,518 B2 | 12/2011 | Turner et al. |
| 8,091,727 B2 | 1/2012 | Domkowwski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 | 8/2012 | Ferlic |
| 8,257,286 B2 | 9/2012 | Meyer et al. |
| 8,328,082 B1 | 12/2012 | Bochenko et al. |
| 8,348,895 B1 | 1/2013 | Vitello |
| 8,353,869 B2 | 1/2013 | Ranalletta et al. |
| 8,413,811 B1 | 4/2013 | Arendt |
| 8,443,999 B1 | 5/2013 | Reinders |
| D684,057 S | 6/2013 | Kwon |
| 8,512,277 B2 | 8/2013 | Del Vecchio |
| 8,528,757 B2 | 9/2013 | Bisio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,910 B2 | 7/2014 | Bauss et al. |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,016,473 B2 | 4/2015 | Tamarindo |
| 9,082,157 B2 | 7/2015 | Gibson |
| 9,101,534 B2 | 8/2015 | Bochenko |
| D738,495 S | 9/2015 | Strong et al. |
| 9,125,976 B2 | 9/2015 | Uber, III et al. |
| D743,019 S | 11/2015 | Schultz |
| 9,199,042 B2 | 12/2015 | Farrar et al. |
| 9,199,749 B1 | 12/2015 | Vitello et al. |
| 9,220,486 B2 | 12/2015 | Schweiss et al. |
| 9,220,577 B2 | 12/2015 | Jessop et al. |
| D750,228 S | 2/2016 | Strong et al. |
| 9,272,099 B2 | 3/2016 | Limaye et al. |
| 9,311,592 B1 | 4/2016 | Vitello et al. |
| D756,777 S | 5/2016 | Berge et al. |
| 9,336,669 B2 | 5/2016 | Bowden et al. |
| D759,486 S | 6/2016 | Ingram et al. |
| D760,384 S | 6/2016 | Niunoya et al. |
| D760,902 S | 7/2016 | Persson |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Ingram et al. |
| D777,903 S | 1/2017 | Schultz |
| 9,662,456 B2 | 5/2017 | Woehr |
| D789,529 S | 6/2017 | Davis et al. |
| 9,687,249 B2 | 6/2017 | Hanlon et al. |
| 9,744,304 B2 | 8/2017 | Swift et al. |
| D797,928 S | 9/2017 | Davis et al. |
| D797,929 S | 9/2017 | Davis et al. |
| 9,764,098 B2 | 9/2017 | Hund et al. |
| 9,821,152 B1 | 11/2017 | Vitello et al. |
| D806,241 S | 12/2017 | Swinney et al. |
| D807,503 S | 1/2018 | Davis et al. |
| 9,855,191 B1 | 1/2018 | Vitello et al. |
| D815,945 S | 4/2018 | Fischer |
| 9,987,438 B2 | 6/2018 | Stillson |
| D825,746 S | 8/2018 | Davis et al. |
| 10,039,913 B2 | 8/2018 | Yeh et al. |
| D831,201 S | 10/2018 | Holtz et al. |
| D834,187 S | 11/2018 | Ryan |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B1 | 2/2019 | Vitello |
| D842,464 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 | 6/2019 | Vitello et al. |
| 10,315,808 B2 | 6/2019 | Taylor et al. |
| 10,376,655 B2 | 8/2019 | Pupke et al. |
| D859,125 S | 9/2019 | Weagle et al. |
| 10,478,262 B2 | 11/2019 | Niese et al. |
| 10,758,684 B1 | 9/2020 | Vitello et al. |
| 10,773,067 B2 | 9/2020 | Davis et al. |
| 10,888,672 B1 | 1/2021 | Vitello |
| 10,898,659 B1 | 1/2021 | Vitello et al. |
| 10,912,898 B1 | 2/2021 | Vitello et al. |
| 10,933,202 B1 | 3/2021 | Banik |
| 10,953,162 B1 | 3/2021 | Hunt et al. |
| 11,040,149 B1 | 6/2021 | Banik |
| 11,040,154 B1 | 6/2021 | Vitello et al. |
| 11,097,071 B1 | 8/2021 | Hunt et al. |
| 11,278,681 B1 | 3/2022 | Banik et al. |

(56) References Cited

U.S. PATENT DOCUMENTS

| | | | |
|---|---|---|---|
| D948,713 S | 4/2022 | Banik | |
| 11,357,588 B1 | 6/2022 | Vitello et al. | |
| 11,413,406 B1 | 8/2022 | Vitello et al. | |
| 11,426,328 B1 | 8/2022 | Ollmann et al. | |
| 11,471,610 B1 | 10/2022 | Banik et al. | |
| 11,523,970 B1 | 12/2022 | Vitello et al. | |
| 11,541,180 B1 | 1/2023 | Vitello et al. | |
| 11,690,994 B1 | 7/2023 | Banik et al. | |
| 11,697,527 B1 | 7/2023 | Hendren et al. | |
| 2001/0056258 A1 | 12/2001 | Evans | |
| 2002/0023409 A1 | 2/2002 | Py | |
| 2002/0046962 A1 | 4/2002 | Vallans et al. | |
| 2002/0079281 A1* | 6/2002 | Hierzer | G09F 19/12 53/410 |
| 2002/0097396 A1 | 7/2002 | Schafer | |
| 2002/0099334 A1 | 7/2002 | Hanson et al. | |
| 2002/0101656 A1 | 8/2002 | Blumenthal et al. | |
| 2002/0104770 A1 | 8/2002 | Shapeton et al. | |
| 2002/0133119 A1 | 9/2002 | Eakins et al. | |
| 2003/0055685 A1 | 3/2003 | Cobb et al. | |
| 2003/0146617 A1 | 8/2003 | Franko, Sr. | |
| 2003/0183547 A1 | 10/2003 | Heyman | |
| 2003/0187403 A1 | 10/2003 | Balestracci | |
| 2004/0008123 A1 | 1/2004 | Carrender et al. | |
| 2004/0064095 A1 | 4/2004 | Vitello | |
| 2004/0116858 A1 | 6/2004 | Heinz et al. | |
| 2004/0173563 A1* | 9/2004 | Kim | B65D 41/48 215/254 |
| 2004/0186437 A1 | 9/2004 | Frenette et al. | |
| 2004/0225258 A1 | 11/2004 | Balestracci | |
| 2005/0146081 A1 | 7/2005 | MacLean et al. | |
| 2005/0148941 A1 | 7/2005 | Farrar et al. | |
| 2005/0209555 A1 | 9/2005 | Middleton et al. | |
| 2006/0084925 A1 | 4/2006 | Ramsahoye | |
| 2006/0089601 A1 | 4/2006 | Dionigi | |
| 2006/0169611 A1 | 8/2006 | Prindle | |
| 2006/0173415 A1 | 8/2006 | Cummins | |
| 2006/0189933 A1 | 8/2006 | Alheidt et al. | |
| 2007/0060898 A1 | 3/2007 | Shaughnessy et al. | |
| 2007/0106234 A1 | 5/2007 | Klein | |
| 2007/0142786 A1 | 6/2007 | Lampropoulos et al. | |
| 2007/0191690 A1 | 8/2007 | Hasse et al. | |
| 2007/0219503 A1 | 9/2007 | Loop et al. | |
| 2007/0257111 A1 | 11/2007 | Ortenzi | |
| 2008/0068178 A1 | 3/2008 | Meyer | |
| 2008/0097310 A1 | 4/2008 | Buehler et al. | |
| 2008/0106388 A1 | 5/2008 | Knight | |
| 2008/0140020 A1 | 6/2008 | Shirley | |
| 2008/0243088 A1 | 10/2008 | Evans | |
| 2008/0303267 A1 | 12/2008 | Schnell et al. | |
| 2008/0306443 A1 | 12/2008 | Neer | |
| 2009/0084804 A1 | 4/2009 | Caspary et al. | |
| 2009/0099552 A1 | 4/2009 | Levy et al. | |
| 2009/0149815 A1 | 6/2009 | Kiel et al. | |
| 2009/0166311 A1 | 7/2009 | Claessens | |
| 2009/0326481 A1 | 12/2009 | Swisher et al. | |
| 2010/0050351 A1 | 3/2010 | Colantonio et al. | |
| 2010/0084403 A1 | 4/2010 | Popish et al. | |
| 2010/0126894 A1 | 5/2010 | Koukol et al. | |
| 2010/0179822 A1 | 7/2010 | Reppas | |
| 2010/0228226 A1 | 9/2010 | Nielsen | |
| 2010/0252564 A1 | 10/2010 | Martinez et al. | |
| 2010/0283238 A1 | 11/2010 | Deighan et al. | |
| 2011/0044850 A1 | 2/2011 | Solomon et al. | |
| 2011/0046550 A1 | 2/2011 | Schiller et al. | |
| 2011/0046603 A1 | 2/2011 | Felsovalyi et al. | |
| 2012/0064515 A2 | 3/2012 | Knapp et al. | |
| 2012/0096957 A1 | 4/2012 | Ochman | |
| 2012/0110950 A1 | 5/2012 | Schraudolph | |
| 2013/0018356 A1 | 1/2013 | Prince et al. | |
| 2013/0056130 A1 | 3/2013 | Alpert et al. | |
| 2013/0088354 A1 | 4/2013 | Thomas | |
| 2013/0237949 A1 | 9/2013 | Miller | |
| 2013/0269592 A1 | 10/2013 | Heacock et al. | |
| 2014/0000781 A1 | 1/2014 | Franko, Jr. | |
| 2014/0034536 A1 | 2/2014 | Reinhardt et al. | |
| 2014/0069202 A1 | 3/2014 | Fisk | |
| 2014/0069829 A1 | 3/2014 | Evans | |
| 2014/0076840 A1* | 3/2014 | Graux | B65D 41/485 215/341 |
| 2014/0135738 A1 | 5/2014 | Panian | |
| 2014/0155868 A1 | 6/2014 | Nelson et al. | |
| 2014/0163465 A1 | 6/2014 | Bartlett, II et al. | |
| 2014/0257843 A1 | 9/2014 | Adler et al. | |
| 2014/0326727 A1 | 11/2014 | Jouin et al. | |
| 2014/0353196 A1 | 12/2014 | Key | |
| 2015/0013811 A1* | 1/2015 | Carrel | A61J 1/1425 137/798 |
| 2015/0048045 A1* | 2/2015 | Miceli | B65D 41/04 215/201 |
| 2015/0112296 A1* | 4/2015 | Ishiwata | B65D 51/002 604/406 |
| 2015/0136632 A1 | 5/2015 | Moir et al. | |
| 2015/0182686 A1 | 7/2015 | Okihara | |
| 2015/0191633 A1 | 7/2015 | De Boer et al. | |
| 2015/0246185 A1 | 9/2015 | Heinz | |
| 2015/0302232 A1 | 10/2015 | Strassburger et al. | |
| 2015/0305923 A1 | 10/2015 | Bochenko | |
| 2015/0310771 A1 | 10/2015 | Atkinson et al. | |
| 2016/0067144 A1 | 3/2016 | Chang | |
| 2016/0067422 A1 | 3/2016 | Davis et al. | |
| 2016/0090456 A1 | 3/2016 | Ishimaru et al. | |
| 2016/0136352 A1 | 5/2016 | Smith et al. | |
| 2016/0144119 A1 | 5/2016 | Limaye et al. | |
| 2016/0158110 A1 | 6/2016 | Swisher et al. | |
| 2016/0158449 A1 | 6/2016 | Limaye et al. | |
| 2016/0176550 A1 | 6/2016 | Viitello et al. | |
| 2016/0194121 A1* | 7/2016 | Ogawa | A61J 1/05 215/249 |
| 2016/0250420 A1 | 9/2016 | Maritan et al. | |
| 2016/0279032 A1 | 9/2016 | Davis | |
| 2016/0328586 A1 | 11/2016 | Bowden et al. | |
| 2016/0361235 A1 | 12/2016 | Swisher | |
| 2016/0367439 A1 | 12/2016 | Davis et al. | |
| 2017/0007771 A1 | 1/2017 | Duinat et al. | |
| 2017/0014310 A1 | 1/2017 | Hyun et al. | |
| 2017/0124289 A1 | 5/2017 | Hasan et al. | |
| 2017/0173321 A1 | 6/2017 | Davis et al. | |
| 2017/0203086 A1 | 7/2017 | Davis | |
| 2017/0225843 A1 | 8/2017 | Glaser et al. | |
| 2017/0239141 A1 | 8/2017 | Davis et al. | |
| 2017/0297781 A1* | 10/2017 | Kawamura | B65D 51/18 |
| 2017/0319438 A1 | 11/2017 | Davis et al. | |
| 2017/0354792 A1 | 12/2017 | Ward | |
| 2018/0001540 A1 | 1/2018 | Byun | |
| 2018/0014998 A1 | 1/2018 | Yuki et al. | |
| 2018/0064604 A1* | 3/2018 | Drmanovic | B65D 43/16 |
| 2018/0078684 A1 | 3/2018 | Peng et al. | |
| 2018/0089593 A1 | 3/2018 | Patel et al. | |
| 2018/0098915 A1 | 4/2018 | Rajagopal et al. | |
| 2018/0147115 A1* | 5/2018 | Nishioka | B65D 51/18 |
| 2018/0312305 A1 | 11/2018 | Rognard | |
| 2019/0308006 A1 | 10/2019 | Erekovcanski et al. | |
| 2019/0388626 A1 | 12/2019 | Okihara | |
| 2022/0008645 A1 | 1/2022 | Ukai et al. | |

\* cited by examiner

TAMPER EVIDENT SEAL FOR A VIAL COVER

The present application is based on and a claim of priority is made under 35 U.S.C. Section 119(e) to a provisional patent application that is in the U.S. Patent and Trademark Office, namely, that having Ser. No. 63/131,124 and a filing date of Dec. 28, 2020, and which is incorporated herein by reference.

BACKGROUND OF THE INVENTION

Field of the Invention

This invention is directed to a closure or cover type of seal structure for a septum or other cover for a vial including a housing disposable in enclosing, retaining engagement with the upper end of the vial and the septum or cover attached thereto. The housing further includes tamper evident capabilities, which prevent reattachment or reuse of the housing in the intended manner.

Description of the Related Art

In the medical field, it is relatively common procedure to administer fluids to a patient by syringes, intravenous infusion (IV), etc. Such administration devices or assemblies are useful in the treatment of a number of medical conditions because a variety of fluids and/or medications can be administered to a patient utilizing such assemblies. By way of example, it is common for medical personnel to order that a patient be given a medication by injection. However, there are a number of safety issues associated with administering injections. One concern relates to avoiding contamination by bacteria, germs, or other harmful organisms. Because of this, and also due to the potential for theft of the medication and/or tampering in order to access the medication, one important concern relates to minimizing the number of people handling syringes. This concern is perhaps even more pronounced with regard to pre-filled syringes.

More specifically it is relatively common in a number of hospital settings for a number of syringes to be pre-loaded or pre-filled with certain medications by pharmacists or other authorized personnel, at an appropriate location, for subsequent dispensing of such prefilled syringes to one or more nursing stations or distribution areas and then, subsequently to the patient for direct use. The pharmacy or location where syringes are filled are often located in a remote part of the health facility relative to the location of the patient and the site of administration of the injection. From the foregoing, it may be understood that during the course of loading a syringe with a drug, and also afterwards when a prefilled syringe is delivered to a nurse's station, the syringe can easily be handled by a number of different individuals. This, in turn, increases the chance for the syringe to become contaminated which in turn, could possibly result in introduction of a contaminated substance into the body tissues of a patient. Consequently, a high level of importance is associated with maintaining the sterility of a syringe, from the time of it being filled to the time of injection administration.

Also, in the case of a very expensive drug or addictive drug such as, but not limited to, morphine, there is some danger that a prefilled syringe will be tampered with by person seeking to improperly gain access to the drug. A resulting danger also exists in the possibility of a saline solution or other substance being substituted for a dose of the medication intended to be administered. This could have extremely serious consequences to the patient, possibly including death. Therefore, the growing use of prefilled syringes raises problems relating to the determination of whether a prefilled syringe has been tampered with and and/or exposed to contamination. In order to address such problems, there is a need in the medical field for closures for syringes and/or other medical containers or administering devices, which maintain sterility while providing sufficient assurances that the contents of the syringe, medical container, administering devices, etc. have not been compromised.

Accordingly, tamper evident capabilities and/or structures associated with medical closures, covers, caps, etc. are important to protect the integrity of prefilled syringes, as well as other types of medical containers. Thus, and as a further example, vials are often filled with a previously prepared medication and are utilized in combination with a syringe. In use, the needle of the syringe penetrates and passes through a septum and into the interior of vial to establish access to the medication contained therein. As is well recognized in the medical profession, vials are medical containers recognized by appropriate governmental bodies and/or legislation (e.g., 503b) and hospital pharmacies for the containment of medications such as, but not limited to, medication prepared for the distribution of vaccines. As such, the open-end or access opening of the vial include a lid crimped or otherwise secured to the open end of the vial, wherein a penetrable septum may be structured as part of the vial lid.

In many cases, vials contain more than one dose of the contained medication or drug. After the first use, medical personnel commonly use tape placed over the septum and other portions of the vial lid to protect the contents of the vial. In other instances, and by way of example, a vial lid can also be utilized with a chemo vent needle, which is used to reconstitute medication at the hospital pharmacy. More specifically, vials used for chemotherapy drugs may contain a powder material. In order to accomplish conversion to a final drug it must be reconstituted, which in turn may involve breaking the original vial lid. To practice the aforementioned procedure, needles are required to prevent any toxic fumes escaping during the preparation and/or conversion. Once preparation is complete, an additional closure, cover, seal, etc. can be applied to the fully converted or prepared medication.

In order to address the problems and disadvantages of the type set forth above, especially with regard to protecting the contents of a vial containing one or more doses and/or the aforementioned chemotherapy medication, there is a need in the medical profession and related supply industries for a cover type seal structured to be secured to the vial and/or lid or cover of the vial in a manner which closes or seals the septum associated with the vial lid or cover. In addition, if any such proposed seal structure were developed, it would preferably also include tamper evident capabilities and/or structure which provides clear evidence that authorized or unauthorized prior access to the vial has been attempted.

SUMMARY OF THE INVENTION

The present invention is directed to a cover or closure type seal structure for a vial and/or vial cover including a housing. The housing includes a sidewall surrounding and at least partially defining the boundaries of the interior of the housing, wherein the interior of the housing is at least partially hollow. In addition, the sidewall terminates in a closed-end and an open-end which are substantially, oppositely disposed to one another. As will be explained in greater detail hereinafter, the open-end is dimensioned and configured to facilitate passage therethrough of the vial and a vial cover or lid, secured to the open-end or access opening of the vial.

Additional features of the seal structure include a retainer disposed within the interior of the housing. In at least one embodiment, the retainer is fixedly or integrally secured to the interior surface of the housing and more specifically, to the interior surface of the sidewall. Also, the retainer extends there-from, inwardly towards the center of the open or hollow interior of the housing. In the one or more preferred embodiments of the retainer, as explained in greater detail hereinafter, it is disposed and structured for retaining engagement with the vial and/or the vial cover or lid.

It is emphasized that the term "vial", as used herein, is meant to include the vial itself as well as the cover or lid secured in overlying relation to the open end thereof. Moreover, as typically structured, the vial cover or lid may include a septum formed of a penetrable material which facilitates passage of a needle of a syringe or other medical device to pass therethrough into direct contact and/or communication with the medication contained within the vial. Accordingly, when describing the retainer being disposed in retaining engagement with the vial it is to be recognized that the actual "retaining engagement" may comprise the retainer being disposed, in whole or in part, in operative engagement with the vial itself or in the alternative with the vial cover and more specifically the periphery thereof, as will be described in greater detail hereinafter.

One or more embodiments of the retainer include it being at least partially defined by a plurality of retainer segments disposed in spaced, substantially coplanar relation to one another and collectively having an annular or circular configuration. As indicated, each of the retainer segments may be fixedly or integrally secured to the interior surface of the sidewall and extend inwardly, substantially towards the center of the hollow interior of the housing. The plurality of retainer segments are cooperatively disposed and structured to establish the aforementioned "retaining engagement" of the retainer with the vial and/or more specifically with an under portion of the outer periphery of the vial cover or lid.

The plurality of retainer segments may vary in size and configuration and may be collectively dimensioned with a remainder of the housing to accommodate a vial and/or vial cover or lid of different sizes. Further, in order to establish the intended "retaining engagement" with the vial each or at least a majority of the retainer segments have a cooperative configuration. In more specific terms, the undersurface portion of each of the retainer segments has a curved or beveled configuration which facilitates a sliding engagement of the vial and/or vial cover or lid with such beveled undersurface. In addition, the sidewall of the housing is structured to include at least a minimal degree of outward flexure. As a result, as the vial and/or vial cover or lid enter through the open end of the housing, they will be forced into the aforementioned sliding engagement with the beveled or curved undersurface portions of each or at least a majority of the plurality of retainer segments. Such forced, sliding engagement will cause at least a minimal outward flexure of the housing, which in turn will allow passage of at least a portion of the vial, such as the vial cover or lid to pass through the retainer and/or plurality of retainer segments and be operatively disposed between the retainer and the inner surface of the closed-end.

The aforementioned retaining engagement is further facilitated by the upper surface of each or at least a majority of the retainer segments being configured to establish an abutting, "removal preventing" engagement with the vial and/or vial cover or lid. More specifically, the upper surface of the one or more retainer segments may be substantially flat or planar and be operatively disposed immediately beneath and in engagement with the under portion of the neck of the vial and/or most probably the undersurface of the outer periphery of the vial cover and/or lid. It is to be noted that both the undersurface and upper surface of the plurality of retainer segments may vary in configuration from that specifically described herein. However, the configurations of the undersurface and the upper surface of the plurality of retainer segments should be sufficient to respectively facilitate the aforementioned sliding engagement of the undersurface of the retainer segments with the vial and the removal preventing engagement of the upper surface.

In addition, and in cooperation with the retainer, one or more preferred embodiments of the seal structure of the present invention further includes a pressure member. The pressure member has an at least minimally elongated configuration fixedly secured to the interior surface of the housing. As such, the pressure member includes a proximal end fixedly or integrally secured to the interior surface of the closed-end and extending downwardly or inwardly therefrom and in depending relation thereto. Moreover, the pressure member includes a distal end substantially oppositely located to the proximal end and in outwardly spaced relation from the interior surface of the closed-end of the housing. The dimension and configuration of the pressure member is cooperatively determined relative to the location and structure of the retainer. Therefore, the distal end of the pressure member is disposed in substantially aligned relation to the retainer and/or plurality of retainer segments so as to be substantially coplanar or minimally spaced out of such a coplanar relation with the retainer.

Accordingly, the pressure member is disposed, configured and structured such that the aforementioned distal end thereof is disposed in a pressure exerting engagement with the vial cover or lid and more specifically with the septum of the vial. Due to the cooperative configurations and dispositions of the retainer and the pressure member, specifically including the distal end of the pressure member, the distal end will be disposed in the aforementioned pressure exerting, at least partially sealing engagement with the vial cover or lid and even more specifically the septum associated with the vial cover or lid. Concurrently the retainer, including the plurality of retainer segments, will be disposed in the retaining engagement comprising the engaging relation with an under portion of the outer periphery of the vial cover or lid. As a result, the vial and more specifically the vial cover or lid will be securely retained on the interior of the housing by virtue of a substantially clamping action and engagement between the retainer and/or plurality of retainer segments and the pressure member and/or distal end thereof exerting pressure on the septum or other portion of the vial cover or lid. Such clamping action will result in a sealing engagement and or action of the vial cover and in particular the sealing, pressure exerting engagement of the distal end of the pressure member with the septum.

With further reference to the pressure member, at least one embodiment includes the provision of an antiseptic or disinfected connected to mounted on or otherwise operatively associated with the distal end. Moreover, the antiseptic, disinfectant or like composition may be on or within a pad, wherein the pad is fixedly secured to the distal end at a location which facilitates its direct engagement with the exterior surface of the septum, during the pressure exerting engagement of the pressure member/distal end with the vial cover. The aforementioned antiseptic pad may be made of a foam or other appropriate cushion-like material in order to engage the septum of the vial cover or lid without causing damage thereto.

As emphasized herein, the seal structure of the present invention includes tamper evident capabilities and/or structure. In at least one embodiment the tamper evident capability or structure includes a removable sidewall section initially integral with a remainder of the sidewall. Further, the removable sidewall section includes a detachable connection to the remainder of the sidewall. Such a detachable connection may comprise at least one, but preferably two elongated weakened seam lines each disposed on a different opposite side of the removable section and extending along a length thereof from the open end to the closed-end of the housing. The weakened seam lines are structured such that exertion of a pulling or other appropriately directed force on the removable section will cause a breakage, disconnection and/or separation of one or both of the weakened seam lines from the remainder of the sidewall, due to at least in part to reduction in the thickness of the sidewall along and entirety or at least a portion of the length of the weakened seam lines. In addition, the aforementioned pulling or other appropriately directed force exerted on the removable sidewall section may be facilitated by the inclusion of a pull tab secured to the removable section preferably at one end thereof coincident with the open end of the housing. The pull tab will extend outwardly from the exterior surface of the sidewall and otherwise be structured to facilitate the gripping or securement thereof by the hand or fingers of a user.

As should be apparent, partial or complete removal of the removable sidewall section will result in an inability to reconnect the replaceable sidewall section with remainder of the housing. As a result, the housing will not be able to be reconnected in its original operative configuration. In turn, the retainer and the pressure member will not be able to be disposed in retaining, clamping, sealing engagement with the vial and/or the vial cover. Clear evidence of authorized or unauthorized prior attempted access to or tampering with the vial will thereby be apparent.

Yet additional features of one or more embodiments of the seal structure of the present invention may include the dimensioning and configuring of the sidewall to include a display field disposed on the exterior surface of the sidewall. In addition, a machine-readable code will be disposed on the display field. The machine-readable code may take a variety of different code configurations or structures including conventional barcode, quick response code (QR), RFID tag, etc. As a result, the code may be an operative part of a tracking system or tracking capabilities associated with the seal structure of the present invention. Such a tracking system or tracking capability may be operative to facilitate the tracking of each such seal structure along a "path of distribution" from an initial point of manufacture, assembly, distribution, etc. to an endpoint such as a location of authorized use. Such a machine-readable code may be on or at least partially within the display field and include visually observable coded indicia providing adequate information or data regarding the origin, structure, utilization, etc. of the seal structure.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

The invention will now be described more fully hereinafter with reference to the accompanying drawings in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Figure 1:
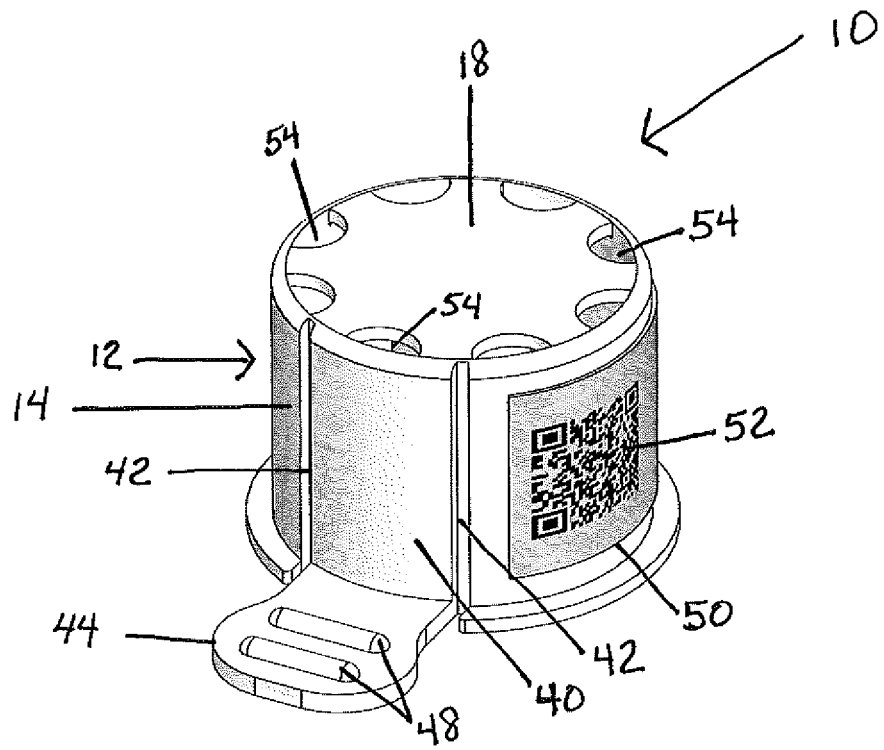
FIG. 1 is a perspective view of a tamper evident seal structure for a vial cover of the present invention.

The present invention is directed to a cover or closure type seal structure generally indicated as 10 for a vial and/or vial cover (not shown in FIG. 1). The seal structure 10 includes a housing generally indicated as 12 having a sidewall 14 surrounding and at least partially defining the boundaries of the interior 16 of the housing 12. The interior 16 of the housing 12 is at least partially hollow, as represented in at least FIGS. 2 and 3. In addition, the sidewall 14 terminates in a closed-end 18 and an open-end 20 which are substantially oppositely disposed to one another. Further, the open-end 20 is dimensioned and configured to facilitate passage therethrough of the vial and a vial cover or lid secured to the open-end or access opening of the vial.

Additional features of the seal structure 10 include a retainer generally indicated as 22 disposed within the interior 16 of the housing 12. In at least one embodiment, the retainer 22 is fixedly or integrally secured to the interior surface 24 of the sidewall and extends therefrom inwardly towards the center of the hollow interior 16 of the housing 12. In one or more embodiments and as will be explained in greater detail hereinafter, the retainer 22 is disposed and structured for retaining engagement with the vial and/or the vial cover or lid.

It is emphasized that the term "vial" as used herein is meant to include the vial itself as well as the cover or lid crimped or otherwise secured in overlying, covering relation to the open end thereof. Moreover, as typically structured, the vial cover or lid may include a septum formed of a penetrable material which facilitates passage of a needle of a syringe or other medical device to pass therethrough into direct contact, access and/or communication with the medication contained within the vial. Accordingly, when describing the retainer 22 being disposed in retaining engagement with the vial, it is to be recognized that the actual "retaining engagement" may comprise the retainer 22 being disposed, in whole or in part, in operative engagement with the vial cover or lid and more specifically the periphery thereof, as described hereinafter.

Figure 2:
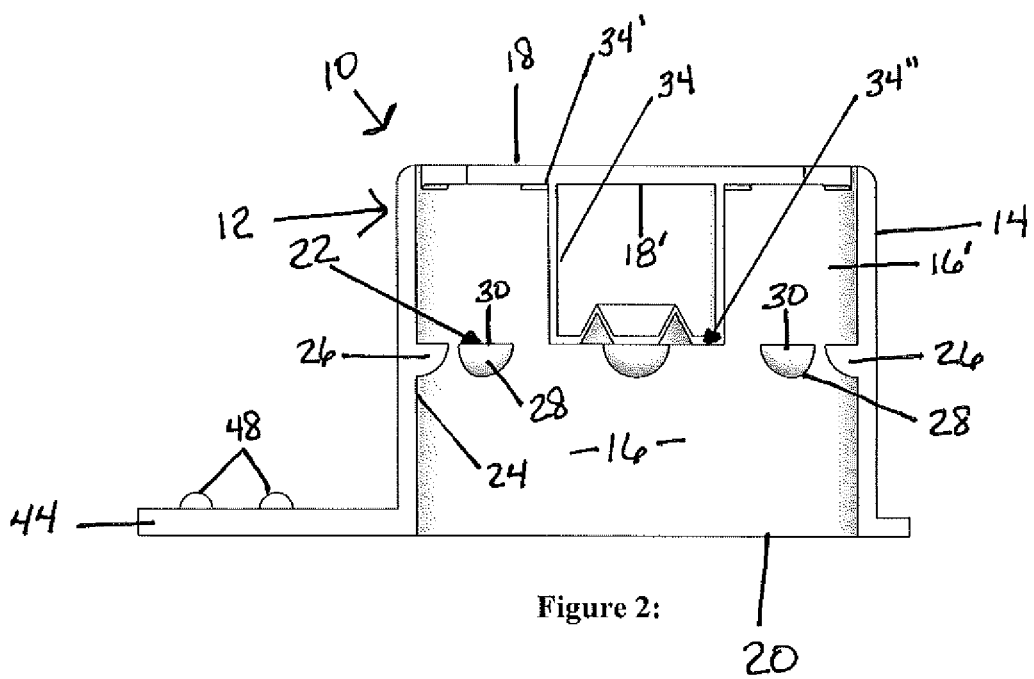
FIG. 2 is an interior sectional view of the embodiment of FIG. 1.
Figure 3:
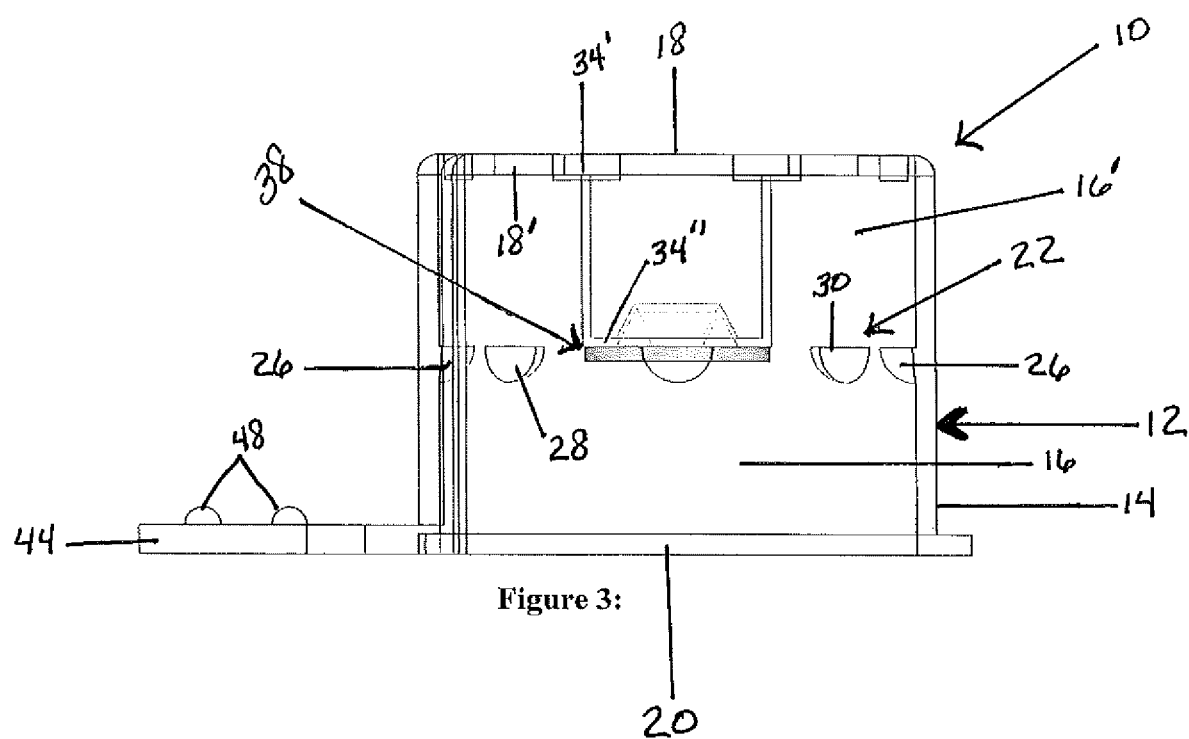
FIG. 3 is an interior sectional view of another preferred embodiment of the present invention including an antiseptic component.

One or more additional embodiments of the retainer 22 include it being at least partially defined by a plurality of retainer segments 26 disposed in spaced relation to one another and collectively having an annular or circular configuration, as represented in FIGS. 2 and 3. As indicated, each of the retainer segments 26 may be fixedly or integrally secured to the interior surface 24 of the sidewall and extend inwardly, substantially towards the center of the hollow interior 16 of the housing 12. The plurality of retainer segments 26 are cooperatively disposed and structured to establish the aforementioned "retaining engagement" of the retainer 22 with the vial and/or more specifically with an under portion of the outer periphery of the vial cover or lid.

The plurality of retainer segments 26 may vary in size and configuration and may be collectively dimensioned with a remainder of the housing 12 to accommodate a vial and/or vial cover or lid of different sizes. Further, in order to establish the intended "retaining engagement" with the vial, each or at least a majority of the retainer segments have a cooperative configuration. In more specific terms, the undersurface portion 28 of each of the retainer segments 26 has a curved or beveled configuration, as represented in FIGS. 2 and 3, which facilitates a sliding engagement of the vial and/or vial cover or lid with such beveled undersurface 28. In addition, the sidewall 14 of the housing is structured to include at least a minimal degree of flexibility in order to facilitate an outward flexure. As a result, as the vial and/or vial cover or lid enter through the open end 20 of the housing 12, it will be forced into the aforementioned sliding engagement with the beveled or curved undersurface portion 28 of each or at least a majority of the plurality of retainer segments 26. Such forced, sliding engagement will cause at least a minimal outward flexure of the sidewall 14 and/or the housing 12, which in turn will allow passage of at least a portion of the vial, such as the vial cover or lid to pass through and beyond the plurality of retainer segments 26 and be operatively disposed with in an interior portion 16' of the housing 12, located between the retainer 22 and the inner surface of the closed-end 18'.

The aforementioned retaining engagement is further facilitated by the upper surface of each or at least a majority of the retainer segments 26 being configured to establish an abutting, "removal preventing" engagement with the vial and/or vial cover or lid. More specifically, the upper surface 30 of the one or more retainer segments 26 may be substantially flat or planar and be operatively disposed immediately beneath and in engagement with the under portion of the neck of the vial and/or most probably the undersurface of the outer periphery of the vial cover and/or lid. It is to be noted that both the undersurface portion 28 and upper surface portion 30 of the plurality of retainer segments 26 may vary in configuration from that specifically described herein. However, the configurations of the undersurface 28 and the upper surface 30 of the plurality of retainer segments should be sufficient to respectively facilitate the aforementioned sliding engagement of the undersurface 28 of the retainer segments 26 with the vial and the removal preventing, abutting engagement of the upper surface 30.

In addition, and in cooperation with the retainer 22, one or more preferred embodiments of the seal structure 10 of the present invention further includes a pressure member 34. The pressure member 34 has an at least minimally elongated configuration fixedly secured to the interior surface of the housing 12. As such, the pressure member 34 includes a proximal end 34' fixedly or integrally or fixedly secured to the interior surface 18' of the closed-end 18 and extending downwardly or inwardly therefrom and in depending relation thereto. Moreover, the pressure member 34 includes a distal end 34" substantially oppositely located to the proximal end 34' and in outwardly spaced relation from the interior surface 18' of the closed-end 18 of the housing 12. The dimension and configuration of the pressure member 34 is cooperatively determined relative to the location and structure of the retainer 22. Therefore, the distal end 34" of the pressure member 34 is disposed in substantially aligned relation to the retainer 22 and/or plurality of retainer segments 26 so as to be substantially coplanar or minimally spaced out of such a coplanar relation with the retainer 22.

Accordingly, the pressure member 34 is disposed, configured and structured such that the aforementioned distal end 34" thereof is disposed in a pressure exerting engagement with the vial cover or lid and more specifically with the septum of the vial lid. Due to the cooperative configurations and dispositions of the retainer 22 and the pressure member 34, specifically including the distal end 34" of the pressure member 34, the distal end 34" will be disposed in the aforementioned pressure exerting, at least partially sealing engagement with the vial cover or lid and the septum associated therewith. Concurrently, the retainer 22, including the plurality of retainer segments 26 will be disposed in the retaining engagement, which comprises the engaging relation of the upper surfaces 30 with an under portion of the outer periphery of the vial cover or lid. As a result, the vial and the vial cover or lid will be securely retained on the interior of the housing 12 by virtue of a substantially clamping action and engagement between the retainer 22 and plurality of retainer segments 26 and the pressure member 34 and distal end 34" thereof exerting pressure on the septum or other portion of the vial cover or lid. Such clamping action will result in a sealing engagement and or action of the vial cover and in particular the sealing, pressure exerting engagement of the distal end 34" of the pressure member 34 with the septum.

With further reference to the pressure member 34 and as represented in FIG. 3, at least one embodiment includes the provision of an antiseptic or disinfectant composition and/or solution operatively associated with the distal end 34". Moreover, the antiseptic, disinfectant or like composition/solution may be on or within a pad 38 which is fixedly secured to the distal end 34" at a location which facilitates the direct engagement of the pad 38 with the exterior surface of the septum, during the pressure exerting engagement of the pressure member 34 or more specifically the distal end 34" with the vial cover.

As emphasized herein, the seal structure 10 of the present invention includes tamper evident capabilities and/or structure. Therefore, in at least one embodiment the tamper evident capability or structure includes a removable sidewall section 40 initially integral with a remainder of the sidewall 14. Further, the removable sidewall section 40 includes a detachable connection to the remainder of the sidewall 14. Such a detachable connection may be defined by and/or comprise at least one but preferably two elongated weakened seam lines 42 each disposed on a different opposite side of the removable section 40 and extending along a length thereof from the open end 20 to the closed-end 18 of the housing 12. The weakened seam lines 42 are structured such that exertion of a pulling or other appropriately directed force on the removable section 40 will cause a breakage, disconnection and/or separation of one or both of the weakened seam lines 42 from the remainder of the sidewall 14, due to at least in part to a reduction in the thickness of the sidewall 14 along and entirety or at least a portion of the length of the weakened seam lines 42. In addition, the aforementioned pulling or other appropriately directed force exerted on the removable sidewall section 40 may be facilitated by the inclusion of a pull tab 44 secured to the removable section 40 preferably at one end thereof which is aligned and/or coincident with the open end 20 of the housing 12. The pull tab 44 is fixedly secured to the removable sidewall section 40 and movable/removable there with as the removable section 40 breaks away from the remainder of the sidewall 14. As represented throughout the Figures, the pull tab 44 will extend outwardly from the exterior surface of the sidewall. To facilitate gripping of the pull tab 44, the exterior surface or other portion of the full tab 44 may be raised, roughened or otherwise structured, as at 48, to facilitate the gripping or securement thereof by the hand or fingers of a user.

As should be apparent, partial or complete removal of the removable sidewall section 40 will result in an inability to reconnect the replaceable sidewall section 40 with remainder of the sidewall 14 or housing 12. As a result, the housing 12 and/or sidewall 14 will not be able to be "closed" or reconnected in its original operative configuration, as represented in at least FIG. 1. In turn, the retainer 22 and the pressure member 34 will not be able to be disposed in retaining, clamping, sealing engagement with the vial and/or the vial cover, as described herein. Clear evidence of authorized or unauthorized prior attempted access to or tampering with the vial will thereby be apparent.

Yet additional features of one or more embodiments of the seal structure of the present invention may include the dimensioning and configuring of the sidewall 14 to include a display field 50 disposed on the exterior surface of the sidewall 14, as clearly represented in FIG. 1. In addition, a machine-readable code 52 will be disposed on or within the display field 50. The machine-readable code 52 may take a variety of different code configurations or structures including a conventional barcode, a quick response code (QR), an RFID tag, etc. As a result, the code 52 may be an operative part of a tracking system or tracking capabilities associated with the seal structure 10 of the present invention.

Yet another structural and operative feature which may be included in at least one embodiment of the seal structure 10 is represented in FIG. 1 and includes at least one but preferably a plurality of openings 54 formed in the closed-end 18 and disposed in communicating relation with the interior 16 and/or 16' of the housing 12.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A seal structure for a vial cover, said seal structure comprising:
   a housing including a sidewall disposed in surrounding relation to an interior of said housing,
   said housing including an open-end and a closed-end oppositely disposed to one another,
   a retainer fixedly disposed on an interior of said housing and structured for retaining engagement with a vial,
   a pressure member disposed within said housing in attached relation to said closed-end,
   said pressure member and said retainer cooperatively disposed in aligned, substantially coplanar relation to one another and concurrently disposed in clamping engagement with the vial cover, and
   said clamping engagement comprising said pressure member disposed in pressure exerting relation to the vial cover concurrent to said retaining engagement of said retainer with the vial cover.

2. The seal structure as recited in claim 1 wherein said retainer is fixedly secured to an inner surface of said housing and extends inwardly therefrom in substantially surrounding relation to said pressure member.

3. The seal structure as recited in claim 2 wherein said retainer comprises a plurality of retainer segments disposed in spaced relation to one another and collectively disposed in substantially surrounding relation to said pressure member.

4. The seal structure as recited in claim 3 wherein each of said plurality of retainer segments includes a substantially beveled undersurface portion, said beveled undersurface portions collectively configured to facilitate sliding engagement of the vial through said retainer, into said retaining engagement.

5. The seal structure as recited in claim 4 wherein each of said plurality of retainer segments include an upper surface configured to prevent passage of the vial out of said retaining engagement and through said open-end.

6. The seal structure as recited in claim 3 wherein each of said plurality of retainer segments include a substantially flat upper surface configured to prevent passage of the vial out of said with retaining engagement and through said open-end.

7. The seal structure as recited in claim 1 wherein said sidewall comprises a removable section, said removable section including a detachable connection to a remainder of said sidewall.

8. The seal structure as recited in claim 7 wherein said detachable connection comprises weakened seam lines disposed on opposite sides of and extending along a length of said removable section, from said open-end to said closed-end.

9. The seal structure as recited in claim 7 further comprising a pull tab, said pull tab fixedly connected to said removable section and removable there with upon detachment of said removable section from a remainder of said sidewall.

10. The seal structure as recited in claim 9 wherein said pull tab is fixedly connected to said removable section at one end thereof adjacent said open-end; said pull tab extending transversely outward from said removable section.

11. The seal structure as recited in claim 9 wherein said detachment of said removable section and said pull tab at least partially defines a tamper evident structure.

12. The seal structure as recited in claim 7 further comprising tamper evident capabilities at least partially defined by a detachment of said removable section from a remainder of said sidewall.

13. The seal structure as recited in claim 1 wherein said sidewall comprises a display field at least partially disposed on an exterior surface thereof, said display field including a machine-readable code.

14. The seal structure as recited in claim 1 wherein said pressure member includes a proximal end fixedly connected to an interior surface of said closed-end and a distal end disposed into said interior of said housing, in spaced, depending relation to said closed-end.

15. The seal structure as recited in claim 1 further comprising an antiseptic composition disposed on said pressure member in engaging relation to the vial cover, concurrent to said clamping engagement with said vial cover.

16. The seal structure as recited in claim 15 wherein said antiseptic composition is disposed on a distal end of said pressure member, in engaging relation to the vial cover, concurrent to said clamping engagement.

17. The seal structure as recited in claim 15 wherein said antiseptic composition comprises an antiseptic composition disposed in a pad, said pad connected to a distal end of said pressure member and disposed in engaging relation to the vial cover, concurrent to said clamping engagement.

18. A tamper evident seal structure for a vial cover comprising:
- a housing including a sidewall disposed in surrounding relation to an interior of said housing,
- said sidewall terminating in an open-end and a closed-end, said closed end oppositely disposed to said open-end,
- said open end dimensioned and configured to receive a vial and a vial cover attached to the vial there through into an interior of said housing,
- a retainer including a plurality of retainer segments each fixedly disposed within said housing and collectively structured for retaining engagement with the vial cover,
- a pressure member connected in depending relation to an interior surface of said closed-end and including a distal end extending into said interior of said housing,
- said pressure member and said plurality of retainer segments cooperatively disposed in aligned, substantially coplanar relation to one another and concurrently disposed in clamping engagement with the vial cover, and
- said clamping engagement comprising said distal end disposed in pressure exerting engagement with the vial cover concurrent to said retaining engagement of said plurality of retainer segments with the vial cover.

19. The seal structure as recited in claim 18 further comprising a tamper evident structure; said tamper evident structure comprising said sidewall including a removable section having a detachable connection to a remainder of said sidewall; said detachable connection comprising at least one weakened seam line disposed on and extending along said removable section, from said open-end to said closed-end.

20. The seal structure as recited in claim 18 further comprising an antiseptic composition disposed on said pressure member in engaging relation to the vial cover, concurrent to said clamping engagement with said vial cover.

* * * * *